United States Patent [19]

Kreyenhagen et al.

[11] Patent Number: 5,152,298
[45] Date of Patent: Oct. 6, 1992

[54] THREADED SUTURE SLEEVE

[75] Inventors: Paul E. Kreyenhagen, Castaic; Jeffrey C. Kristiansen, Simi Valley, both of Calif.

[73] Assignee: Siemens Pacesetter, Inc., Sylmar, Calif.

[21] Appl. No.: 686,095

[22] Filed: Apr. 16, 1991

[51] Int. Cl.⁵ .................................................. A61N 1/00
[52] U.S. Cl. ..................................... 128/784; 604/175
[58] Field of Search ................ 128/784; 604/283, 29, 604/175; 285/332, 386

[56] References Cited

U.S. PATENT DOCUMENTS

| | | | |
|---|---|---|---|
| 4,276,882 | 7/1981 | Dickhudt et al. | 128/419 P |
| 4,387,727 | 6/1983 | Sandstrom | 128/784 |
| 4,516,584 | 5/1985 | Garcia | 128/785 |
| 4,526,572 | 7/1985 | Donnan et al. | 604/283 |
| 4,538,623 | 9/1985 | Proctor et al. | 128/784 |
| 4,553,961 | 11/1985 | Pohndorf et al. | 128/784 |
| 4,629,455 | 12/1986 | Kanno | 604/283 |
| 4,672,979 | 6/1987 | Pohndorf | 128/784 |
| 4,683,895 | 8/1987 | Pohndorf | 128/784 |

Primary Examiner—Stephen C. Pellegrino
Assistant Examiner—Gary Jackson
Attorney, Agent, or Firm—Malcolm J. Romano

[57] ABSTRACT

A suture sleeve for anchoring the lead body of an implantable medical device, such as a cardiac pacemaker, includes an elongated tubular member having a lumen for receiving the lead body. The tubular member has external threads for receiving a threaded collar. The tubular member and collar have engaging, tapered surfaces whereby tightening of the collar on the tubular member compresses a portion of the tubular member into gripping engagement with the lead body. The tubular member and collar have surfaces which come into contact upon tightening of the collar so as to limit compression of the lead body and thereby prevent damage thereto.

9 Claims, 1 Drawing Sheet

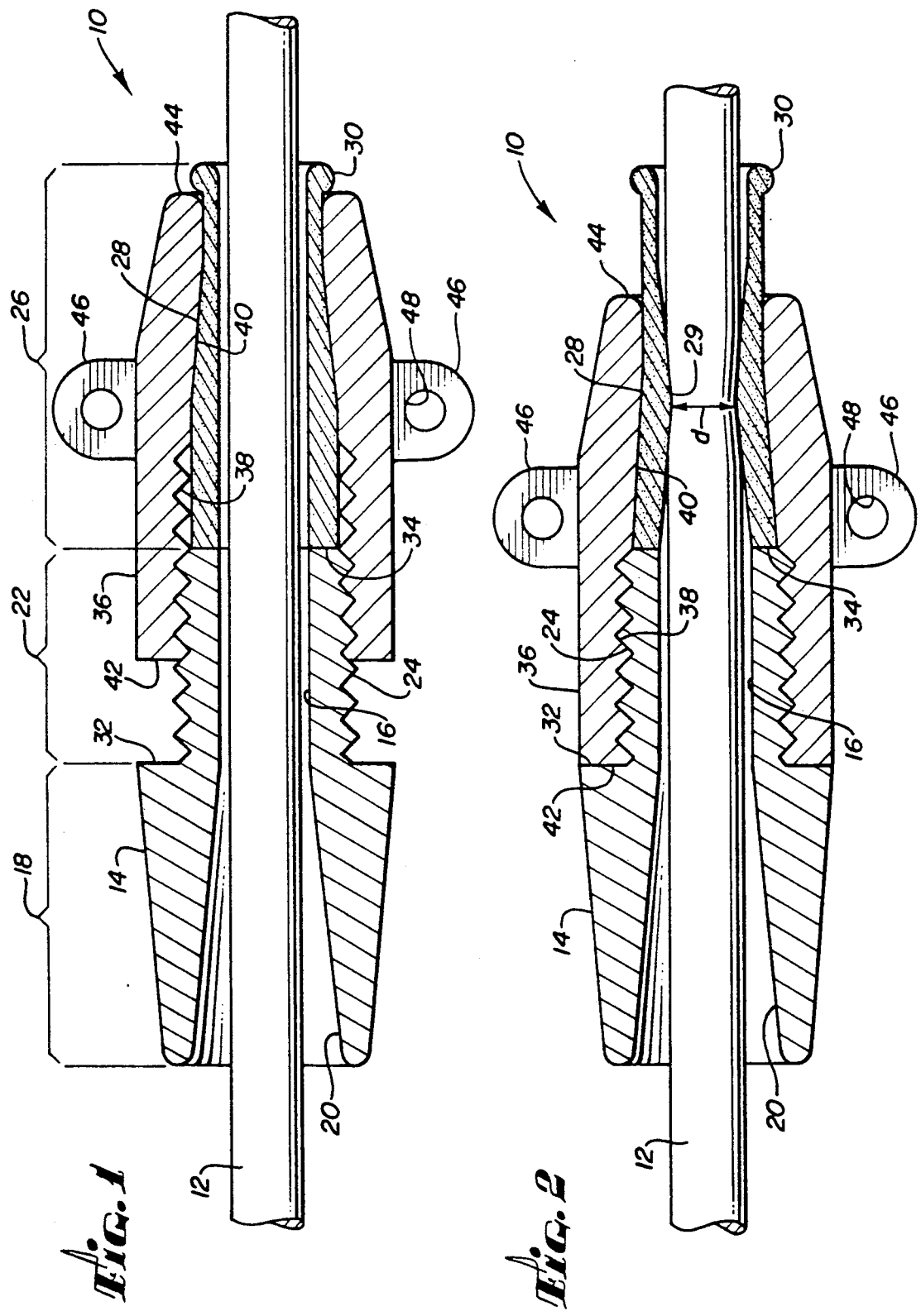

THREADED SUTURE SLEEVE

FIELD OF THE INVENTION

This invention relates generally to suture sleeves for anchoring the lead bodies of implantable medical devices and more particularly to a suture sleeve for securely gripping a lead body while preventing damage thereto.

BACKGROUND OF THE INVENTION

During the implantation of an endocardial lead body, the lead is introduced into the heart using a venous approach, usually from the subclavian or cephalic vein in the shoulder area under the pectoral muscle. To keep the lead body from shifting in the vein, the lead body is secured to both the vein and to the underlying muscle tissue. A suture placed around the vein near the lead entry point ties the lead to the vein, and a suture sleeve around the lead body is used to anchor the lead body to adjacent tissue.

Suture sleeves in present use are generally tubular structures molded out of a soft, implantable elastomer such as silicone. After the lead is tied to the vein, the sleeve is slid along the vein to the location at which the lead is to be anchored to the underlying tissue. One or more sutures are then tied around the sleeve to compress it and thereby secure it to the lead body. Circumferential grooves in the outer surface of the sleeve are typically provided for this purpose. The last step is to anchor the sleeve to adjacent body tissue; sutures passed through eyelets formed in a pair of tabs projecting from the sleeve provide the required anchoring.

Existing suture sleeves have several drawbacks. For example, it is difficult for the physician to control the degree to which these sleeves are compressed when they are secured to a lead body. The ligature around the sleeve must be tight enough to prevent the lead body from sliding in the suture sleeve but not so tight as to damage the insulation of the lead body. This is especially important with bipolar coaxial leads because an excessively tight ligature could rupture the lead insulation and cause the outer and inner electrical leads to come into contact with each other, resulting in a short circuit. It would therefore be desirable to eliminate the need for sutures for compressing the sleeve.

Accordingly, it is an object of the present invention to provide a suture sleeve for securely gripping and anchoring the lead body of an implantable medical device, such as a cardiac pacemaker, that does not require the use of sutures to compress the sleeve.

It is another object of the present invention to provide a lead body gripping and anchoring suture sleeve in which the compression of the sleeve is self-limiting so as to prevent lead body damage.

SUMMARY OF THE INVENTION

In accordance with the broad aspects of the present invention, there is provided a suture sleeve eliminating the need for compression sutures.

In accordance with a preferred embodiment of the invention, the suture sleeve includes a tubular member having a lumen for receiving a lead body. The tubular member has external threads for receiving a mating, internally threaded collar. The tubular member and collar are so configured that the collar, when tightened on the sleeve, radially compresses a portion of the sleeve into gripping engagement with the lead body. The sleeve includes an abutment surface engaged by an end surface of the collar, thereby limiting the travel of the collar and the gripping action imposed thereby. In this fashion, the compression of the lead body is positively controlled so that while providing an adequate degree of gripping, the compression of the lead body is limited, thereby preventing damage thereto.

BRIEF DESCRIPTION OF THE DRAWINGS

Further objects, advantages and features of the invention will become apparent from the detailed description of the preferred embodiments below, when read in conjunction with the accompanying drawing, in which:

FIG. 1 is an axial cross section of a suture sleeve for anchoring the lead body of an implantable medical device in accordance with a preferred embodiment of the present invention, the suture sleeve being shown in its open configuration; and FIG. 2 is an axial cross section of the sleeve of FIG. 1 shown in its closed, lead body-gripping configuration.

DETAILED DESCRIPTION OF THE PREFERRED EMBODIMENT

The drawing shows a suture sleeve 10 for gripping and anchoring the lead body 12 of an implantable medical device such as a cardiac pacemaker. Because the structure of lead bodies is well known in the art, the details thereof have been omitted from the drawings for the sake of simplicity.

The suture sleeve 10 includes an elongated tubular member 14 defining a longitudinal lumen 16 through which the lead body 12 extends. The tubular member 14 has three sections: a first section 18 defining a gently tapered portion 20 of the lumen 16 to facilitate lead body insertion; a second or mid section 22 having threads 24 on the outer surface thereof; and a third section 26 having an outer tapered surface 28 and an enlarged annular end 30. At the junction of the first and second sections is an annular shoulder or abutment surface 32.

The third section 26 of the tubular member 14 is made of a soft implantable elaster, such as silicone or polyurethane, while the remainder of the tubular member is preferably fabricated of relatively hard but flexible implantable plastic, such as polysulfone or acetal resin. A common acetal resin is sold under the name Delrin, which is a registered trademark of E.I. du Pont de Nemours & Co. (Inc.). The soft and hard plastic portions of the tubular member 14 are bonded at an interface 34 using techniques well known in the art.

Disposed about the tubular member 14 and bridging the second and third sections thereof is a collar 36 a portion of which has internal threads 38 received by the threads 24 on the tubular member 14. For a .065-inch diameter outer insulation on the lead body, the preferred thread is 8-36 UNF.

The remaining portion of the collar 36 has a tapered inner wall 40 in engagement with the tapered surface 28 on the tubular member. The tapered inner wall 40 and surface 28 preferably have substantially corresponding slopes. The collar further has a radially extending end surface 42 facing the abutment surface 32 on the tubular member, and an opposite end 44.

A pair of projecting tabs 46 formed integrally with the collar have eyelets 48 adapted to receive sutures (not shown) for tying the suture sleeve to the surrounding tissue.

The collar 36 is preferably made of hard implantable plastic, such as polysulfone or delrin, by way of example. Alternatively, the collar 36 may be fabricated of an implantable metal or metallic alloy such as titanium, platinum, platinum-iridium or stainless steel.

In use, the suture sleeve 10 is initially in the open configuration shown in FIG. 1 in which, by way of example, the collar 36 is open by about three turns.

In this initial, open configuration the end 44 of the collar 36 is in engagement with the enlarged end 30 which thereby functions as a stop to prevent further unscrewing of the collar. In its open configuration, the suture sleeve 10 can move freely on the lead body for proper placement. When the sleeve location has been determined, tightening of the threaded collar 36 on the threads of the tubular member 14 causes the tapered wall 40 of the collar, acting in cooperation with the tapered surface 28 on the tubular member, to compress a portion 29 of the soft section 26 of the tubular member. This action forces the portion 29 inwardly to securely grip the lead body 12, as shown in FIG. 2. Engagement of the end surface 42 of the collar with the abutment surface 32 on the tubular member limits the tightening of the collar, thereby limiting compression of the lead body. Because compression of the lead body insulation is thereby limited, the suture sleeve 10 is designed to provide reliable, secure gripping of the lead body while preventing damage thereto.

More specifically, when the soft plastic section 26 of the tubular member 14 is deformed by tightening the threaded collar 36 until it engages the abutment surface 32, the diameter of the lumen at the compressed portion 29 decreases to a predetermined minimum size "d" (FIG. 2). This dimension is selected so that compression of the lead body does not crush the coil just inside the outer insulation of the lead body.

By making the diameter of the lumen 16 substantially the same as the diameter of the outer insulation of the lead body 12, sliding of the suture sleeve 10 in the open configuration when the lead body is held in a vertical position is prevented.

While various modification and alternative constructions of the invention will be obvious to those skilled in the art, only a specific, preferred embodiment thereof has been shown in the drawings and described in detail. It should be understood, however, that there is no intention to limit the invention to the specific form or example illustrated and described. On the contrary, the intention is to cover all modifications, alternative constructions and equivalents falling within the spirit and scope of the invention as defined by the appended claims.

What is claimed is:

1. A suture sleeve for anchoring the lead body of an implantable medical device, the sleeve comprising:
   a tubular member having an inner surface defining a lumen for receiving the lead body, and an outer surface including a threaded section and a tapered portion;
   a collar disposed about the tubular member coaxially therewith, the collar having internal threads received by the threaded section of the tubular member and an internal wall having a tapered portion engaging the tapered portion of the tubular member, whereby tightening of the threaded collar onto the threaded section of the tubular member causes the tapered portion of the collar to force the tapered portion of the tubular member inwardly to grip the lead body; and
   means for attaching the sleeve to adjacent tissue.

2. A suture sleeve, as defined in claim 1, in which:
   the tubular member has an annular, projecting surface; and
   the collar has an end for engaging said annular surface when the collar is tightened, thereby limiting the tightening of the collar on the tubular member to limit compression of the lead body and prevent damage thereto.

3. A suture sleeve, as defined in claim 1, in which:
   the tubular member has a stop adapted to be engaged by the collar to prevent removal of the collar from the tubular member.

4. A suture sleeve, as defined in claim 1, in which:
   at least the tapered portion of the tubular member comprises soft plastic.

5. A suture sleeve, as defined in claim 4, in which:
   the collar and at least the threaded section of the tubular member comprise a hard but flexible plastic.

6. A suture sleeve, as defined in claim 1, in which:
   the tapered portions of the collar and tubular member has substantially corresponding slopes.

7. A suture sleeve for use in combination with a lead body, the suture sleeve comprising:
   a tubular member having a lumen for receiving the lead body;
   a collar disposed abut the tubular member coaxially therewith, the tubular member and collar having corresponding, mating threaded portions and tapered portions, whereby tightening of the collar onto the threaded portion of the tubular member compresses the tapered portion of the tubular member into engagement with the lead body; and
   the tubular member and collar having means for limiting the tightening of the collar for limiting compression of the lead body for preventing damage to the lead body.

8. A suture sleeve for use in combination with a lead body, the sleeve comprising:
   a tubular member having an inner surface defining a lumen for receiving the lead body, and an outer surface including a threaded section and a deformable tapered portion; and
   a collar disposed about the tubular member coaxially therewith, the collar having internal threads received by the threaded section of the tubular member and an internal wall having a tapered portion engaging the tapered portion of the tubular member, whereby tightening of the threaded collar onto the threaded section of the tubular member causes the tapered portion of the collar to force the tapered portion of the tubular member to deform inwardly to thereby grippingly engage the lead body.

9. A suture sleeve for use in combination with a lead body, the sleeve comprising:
   a tubular member having an inner surface defining a lumen for receiving the lead body and an outer surface including a threaded section and a tapered portion; and
   a collar disposed abut the tubular member coaxially therewith, the collar having internal threads received by the threaded section of the tubular member, the collar tightenable on the threaded section of the tubular member between open and closed positions, the collar further having an internal wall having a tapered portion engaging the tapered portion of the tubular member, the threaded collar being in the closed position compresses the tapered portion of the tubular member to thereby grip the lead body, whereas the threaded collar being in the open position decompresses the tapered portion of the tubular member to thereby release the grip on the lead body.

* * * * *